US007777882B2

United States Patent
Logothetidis

(10) Patent No.: US 7,777,882 B2
(45) Date of Patent: Aug. 17, 2010

(54) METHOD FOR THE IN-SITU AND REAL-TIME DETERMINATION OF THE THICKNESS, OPTICAL PROPERTIES AND QUALITY OF TRANSPARENT COATINGS DURING THEIR GROWTH ONTO POLYMERIC SUBSTRATES AND DETERMINATION OF THE MODIFICATION, ACTIVATION AND THE MODIFICATION DEPTH OF POLYMERIC MATERIALS SURFACES

(76) Inventor: Stergios Logothetidis, Aristotle University of Thessaloniki Physics Department, Thessaloniki 54 124 (GR)

( * ) Notice: Subject to any disclaimer, the term of this patent is extended or adjusted under 35 U.S.C. 154(b) by 256 days.

(21) Appl. No.: 11/920,465

(22) PCT Filed: Jul. 24, 2006

(86) PCT No.: PCT/GR2006/000035

§ 371 (c)(1),
(2), (4) Date: Nov. 15, 2007

(87) PCT Pub. No.: WO2007/015115

PCT Pub. Date: Feb. 8, 2007

(65) Prior Publication Data
US 2009/0103092 A1 Apr. 23, 2009

(30) Foreign Application Priority Data
Aug. 1, 2005 (GR) .............................. 20050100404

(51) Int. Cl.
*G01J 4/00* (2006.01)

(52) U.S. Cl. ...................................... 356/369; 356/630
(58) Field of Classification Search ....................... None
See application file for complete search history.

(56) References Cited

U.S. PATENT DOCUMENTS

| 5,131,752 | A | 7/1992 | Yu et al. ...................... 356/369 |
| 5,277,747 | A | 1/1994 | Aspnes ........................ 156/626 |
| 6,781,692 | B1 | 8/2004 | Rosencwaig ................ 356/369 |

OTHER PUBLICATIONS

Meyer-Pittroff et al., On line control of transparent inorganic layers deposited on polymeric substrate by phase modulated spectroscopic ellipsometry, Feb. 2, 2006, Technische Universitat Munchen, full document.*

(Continued)

*Primary Examiner*—Gregory J Toatley, Jr.
*Assistant Examiner*—Juan D Valentin
(74) *Attorney, Agent, or Firm*—Adams & Wilks

(57) ABSTRACT

This invention concerns the in-situ and real-time determination of thickness, optical properties and quality of transparent inorganic thin films (oxides, nitrides) and organic materials during their growth and during modification of transparent polymeric materials, with the use of Spectroscopic Ellipsometry, with measurements in the spectral region of Vis-FUV from 1.5-6.5 eV, and IR from 0.1-0.49 eV (900-4000 $cm^{-1}$). This method can be used in-line for the monitoring and/or control of the processes in air and in vacuum, that concern substrates on which the thin films will be grown, and of the growth processes of transparent oxides, nitrides and other inorganic and organic films with final result the production of integrated systems with desirable properties.

3 Claims, 14 Drawing Sheets

OTHER PUBLICATIONS

Logothetidis et al., Optical and compositional studies of SiN thin films with conventional and synchrotron radiation ellipsometry, Jun. 15, 1993, American Institue of Physics—J Applied Physics, 73 (12), pp. 8514-8518.*

Vignoli et al., Structural properties depicted by optical measurements in hydrogenated polymorphous silicon, 1999, IOP Publising—J. Phys.: Condens. Matter II, pp. 8749-8757.*

Laskarakis A et al: "FTIR and Vis-FUV real time spectroscopic ellipsometry studies of polymer surface modifications during ion beam bombardment" Nuclear Instruments & Methods in Physics Research, Section—B: Beam Interactions With Materials and Atoms, Elsevier, Amsterdam, NL, vol. 216, Feb. 2004, pp. 131-136, XP004489491 ISSN: 0168-583X.

Kechagias V G et al: "'Real-time' multiwavelength ellipsometry diagnostics for monitoring dry etching of Si and TiNx deposition" Thin Solid Films, Elsevier-Sequoia S.A. Lausanne, CH, vol. 364, No. 1-2, Mar. 2000, pp. 213-219, XP004195098 ISSN: 0040-6090.

Logothetidis S et al: "Real-time monitoring, growth kinetics and properties of carbon based materials deposited by sputtering" Diamond and Related Materials, Elsevier Science Publishers, Amsterdam, NL. vol. 10, No. 2, Feb. 2001, pp. 117-124, XP004322348 ISSN: 0925-9635.

Gioti M et al: "IR-FUV ellipsometry studies on the optical, electronic and vibrational properties of polymeric membranes" Preparation and Characterization, Elsevier Sequoia, NL, vol. 455-456, May 1, 2004, pp. 283-287, XP004504795 ISSN: 0040-6090.

Logothetidis S et al: "In situ and real-time ellipsometry diagnostic techniques towards the monitoring of the bonding structure and growth kinetics: silicon oxide coatings" Surface & Coatings Technology Elsevier Switzerland, vol. 151-152, Mar. 1, 2002, pp. 204-208, XP008069343 ISSN: 0257-8972.

* cited by examiner

United States Patent US 7,777,882 B2

METHOD FOR THE IN-SITU AND REAL-TIME DETERMINATION OF THE THICKNESS, OPTICAL PROPERTIES AND QUALITY OF TRANSPARENT COATINGS DURING THEIR GROWTH ONTO POLYMERIC SUBSTRATES AND DETERMINATION OF THE MODIFICATION, ACTIVATION AND THE MODIFICATION DEPTH OF POLYMERIC MATERIALS SURFACES

CROSS-REFERENCE TO RELATED APPLICATIONS

This application is a U.S. national stage application of International Application No. PCT/GR2006/000035, filed Jul. 24, 2006, claiming a priority date of Aug. 1, 2005, and published in a non-English language.

TECHNICAL FIELD

Industry has detected the necessity for monitoring the manufacturing (or production) processes in real-time, the minimization of time required for production control, as well as the minimization of product losses and failures and production cost. This invention concerns the determination of the thickness, optical properties and quality of transparent inorganic thin films (oxides, nitrides) and organic materials during their growth and the modification/activation of the surfaces of transparent polymeric materials in-situ and real-time with the use of Spectroscopic Ellipsometry (SE) with measurements in the spectral region of Vis-farUV (1.5-6.5 eV) and IR, (0.1-0.49 eV, or 900-4000 cm$^{-1}$). This method can be used in-line for the monitoring and/or control of the production processes (in air and in vacuum), that concern substrates on which the thin films will be grown, and of the growth processes of transparent oxides, nitrides and other inorganic and organic films with final result the production of integrated systems (such as multilayers of inorganic and organic materials) with desirable properties.

REFERENCE TO THE BACKGROUND ART

Spectroscopic Ellipsometry is a non destructive optical technique that is based on the measurement of the change of the light polarization state and provides information for the optical, and not only, materials properties. Spectroscopic Ellipsometry can be used for the in-situ and real-time monitoring during growth of inorganic and organics thin films, for the determination of the mechanisms that take place during growth and for the change of optical properties and substrate properties under various processes.[1]

In semiconductors, insulators but also in metals, bonded electrons with the absorption of a photon from electromagnetic radiation, are excited or undergo interband transitions, which are responsible for the strong absorption in the Vis-FTV spectral region. The application of Spectroscopic Ellipsometry technique, with the use of Synchrotron radiation, gave the possibility of spectroscopic measurements in an energy range up to 9.5 eV, that could not be covered with compatible light sources that are used in lab scale and the verification of the absorption and electronic structure of oxides and transparent materials in FUV spectral area[2-3] Thus, spectroscopic study of materials that show optical transparency in the area of Visible and Near Ultraviolet, such as Silicon Nitride (SiN$_x$), was realized.[2] Moreover in combination with techniques that are used for the determination of the materials composition, the correlation of optical constant and properties was determined. Optical quantities, such as the energy in which appears the maximum electronic absorption in a composite material, known as mean Gap or Penn Gap (E$_0$), and the energy where the edge of electronic absorption appears, known as the fundamental optical energy gap (E$_g$), are the ones that are directly related with their composition. [2-3]

The correlation of optical constants, determined by Spectroscopic Ellipsometry, with other important properties, such as stoichiometry, has been certified also for metallic composite films such as Titanium Nitride films (TiN$_x$), for which the plasma energy $\omega_p$ is correlated with the stoichiometry x. [4-5] The $\omega_p$ is calculated from the Spectroscopic Ellipsometry spectra in the energy region of the dielectric function and is the energy for which the real part of the dielectric function is equal to zero [$\epsilon_1(\omega=\omega_p)=0$]. With the application of in-situ and real-time ellipsometry in the area of visible and Near Ultraviolet, during TiN$_x$ films growth, it was possible the real-time determination of the stoichiometry and thickness of the films TiN$_x$.

Moreover, with application of in-situ and real-time ellipsometty in the area of Infrared, during transparent films Silicon Oxide (SiO$_x$) growth on substrates of crystalline Si, the determination of deposition rate was realised. [6]

Methods for the control in production line of thin films and coatings with priority in the properties of the surfaces, interfaces and layers or thin films that are related to the functional properties of the intermediate and final products are not available aid do not represent existing technologies. The lack of control systems in production line that would be used for the modification and the deposition of thin films onto polymeric surfaces, in combination with the fact that there is transfer of the quality control from the control of the final product to the control during production, requires the improvement of production line performance. This is very important since the deposition processes is comprised of several stages (e.g. surface modification/activation, inorganic or organic coating deposition). Therefore, an appropriate, smart and reliable control process must: a) control the technical requirements for coatings (e.g. good adhesion of the substrate) in new applications, b) provide material and energy reduction and c) keep low the cost of combined processes.

SUMMARY OF THE INVENTION

Method for real-time determination of thickness, optical properties and quality of transparent inorganic thin films (oxides, nitrides) and organic materials during their growth on polymeric or other transparent substrates. For the real-time calculation of the thickness, optical and other properties, during the growth of a transparent film on a transparent substrate, takes place the acquisition of experimental data of the dielectric function with the use of Spectroscopic Ellipsometry (SE) or in real-time with a unit that simultaneously acquires many measurements in various wavelengths (Fast Multiwavelength Ellipsometry-FMWE) adapted in a Ultra High Vacuum Chamber. During the experimental methodology, we have the following stages:

(a) Cover of the necessary energy range with extension of the energy range to the Far Ultraviolet, so that the measurements are performed in the spectral range in the Visible-far UltraViolet (Vis-FUV) for example from 1.5-6.5 eV or 190-830 nm, and in IR, from 0.1-0.49 eV (900-4000 cm$^{-1}$)

(b) Collection of experimental data with the simultaneous measurement, e.g. 32 different wavelengths, that cover the energy range 1.5-6.5 eV and that represent acquisition of the dielectric function spectra, simultaneously and in short time in the range of ms.

(c) Application of the analysis model of the experimental spectra of multi wavelengths for the deduction of the optical parameters and constants of the grown transparent films. Thus the parameterization and analysis of the measured dielectric function <∈(E)> has been performed with the use of a geometrical three phase model (air/thin film/polymeric substrate) where the optical properties of each phase were described by using the modified Tauc-Lorentz model (TL).[7]

This new methodology was applied in deposition processes of thin and transparent oxides on semiconducting but also polymeric substrates, as well as in pretreatment processes of polymeric substrates for the activation of their surfaces, on which later are grown transparent thin films such as Silicon Oxide ($SiO_x$), Titanium Oxide ($TiO_x$), Silicon Nitride ($SiN_x$) for various technological applications.

From the methodology that is applied:

i) the thickness and deposition rate of transparent films are determined with high accuracy. The use of the geometrical model consisted by three phases (air/thin film/polymeric substrate) in the analysis of the SE spectra deducted during oxide deposition, provides the ability to determine the thickness d of the transparent inorganic (oxide, nitride, etc) and organic film. With this analysis, the stability and effectiveness of the deposition processes can be controlled and monitored.

ii) the deposition processes of the transparent oxides films are monitored in real-time.

iii) the optical constants and properties, through which the stoichiometry, composition, and quality of films and substrates are determined. More specifically, the Penn gap $E_0$ and the refractive index n(E=0), are the most important parameters that are determined from the analysis. For example, the $E_0$ is related to the stoichiometry x of the film, while the quantity n (E=0) is related with the stoichiometry and with the quality of oxides and nitrides thin films (that is related with the existence of voids and defects). All the other parameters provide indirect information for the quality of deposited films.

iv) the barrier properties in gases and vapors of the system thin film/polymeric substrate are determined. This determination is the result of the correlation between the optical and other properties of the system that were measured in real-time with the above mentioned methodology (e.g. stoichiometry x) with Oxygen (OTR) and Water Vapor Transmission measurements (WVTR). For the exact correlation among optical and final functional properties there is use of the refractive index n (E=0) and of the Penn gap $E_0$.

v) determination of the thickness of the surface layer that is formed with the ion bombardment (or in plasma conditions) of the polymeric substrates in vacuum. Depending on the experimental conditions that are applied and on the properties of this surface layer, it is determined the activation of the polymeric surface and the adhesion properties between the interface of the polymeric substrate and the grown thin film.

In overall, the methodology that has been developed can be used in-line for the monitoring and control of the various vacuum processes of the substrates on which the thin films will be grown, and for the growth process of transparent inorganic (oxides and nitrides) or and organic films, to finally result in the production of complete systems, with desirable properties. This is especially important for the control of production & manufacturing processes in real-time and for the minimization of the time needed for production control, of the losses and of the production cost.

Methods for the control in production line of thin films and coatings with priority in the properties of the surfaces, interfaces and layers or films that are related to the functional properties of the intermediate and final products are not available and do not represent existing technologies. The lack of control systems in production line for the modification and coating of polymeric surfaces and in combination with the fact that there is transfer of the quality control from the control of the final product to the control during production requires the improvement of production line performance. This is very important since the coating deposition processes is comprised of several stages (e.g. surface functionalization, inorganic or organic coating deposition). Therefore, an appropriate, smart and reliable control process must: (a) control the technical requirements for coatings (e.g. good adhesion of the substrate) in new applications, (b) provide consumer materials and energy reduction and (c) remain the cost of combined processes low.

[1] "THIN FILMS HANDBOOK: Processing, Characterization and Properties" in "In-situ monitoring in thin films during growth with Spectroscopic Ellipsometry"
S. Logothetidis, ed. by Hari Singh Nalwa (Academic Press, 2001).

[2] "Optical and compositional studies of SiN thin films with conventional and synchrotron radiation ellipsometry"
S. Logothetidis, J. Petalas, A. Markwitz and R. L. Johnson
*J. Appl. Phys.* 73, 8514 (1993).

[3] "Characterization of SiN thin films with spectroscopic ellipsometry"
J. Petalas, S. Logothetidis, A. Markwitz, E. C. Paloura, R. L. Johnson and D. Fuchs
*Physica B*185, 342 (1993).

[4] "$TiN_x$ thin films deposited by reactive magnetron sputtering: in-situ monitoring and effect of deposition parameters"
S. Logothetidis, and J. Alexandrou
*J. Mechan. Behav. of Mater.* 6, 33 (1995).

[5] "New approach in the monitoring and characterization of titanium nitride thin films"
S. Logothetidis, E. I. Meletis, and G. Kourouklis
*J. Mater. Res.* 14, 436 (1999).

[6] "In situ and real-time ellipsometry diagnostic techniques towards the monitoring of the bonding structure and growth kinetics: silicon oxide coatings"
S. Logothetidis, A. Laskarakis, A. Gika, and P. Patsalas
*Surf and Coat. Technol* 151-152, 204 (2002).

[7] G. E. Jellison, F. A. Modine, Appl. Phys. Lett. 69 (1996) 371.

DETAILED DESCRIPTION OF THE INVENTION

A. General

In this unit, is described the method for acquiring SE spectra in situ and real-time in the range of ms for the case of the following examples: a) surface treatment of PET polymeric substrate with the use of ion bombardment with $N_2$ gas and b) growth of thin film oxides $SiO_x$ on polymeric substrate Poly (Ethylene Terephthalate) (PET) with the of e-beam evaporation technique or other Physical or Chemical Vapor Deposition techniques (PVD or CVD). This methodology can be generally applied in the case of monolayered and multilayered, transparent and non-transparent thin films, that can be comprised only of (or combination of) thin films of Silicon Oxide ($SiO_x$), Titanium Oxide ($TiO_x$), Silicon Nitride ($SiN_x$), Titanium Nitride ($TiN_x$), Zinc Oxide ($ZnO_x$), Boron Nitride ($BN_x$), Carbon Nitride ($CN_x$), Aluminium Oxidev ($AlO_x$) for all the stoichiometry values x that are developed with the various Physical and Chemical Vapor Deposition growth techniques, such as magnetron sputtering (dc, rf or/and reactive), e-beam evaporation, ion beam sputtering, ion beam assisted deposition, CVD, Plasma Enhanced CVD, laser ablation, laser deposition. Moreover, it can be applied for all polymeric substrates such as Poly(Ethylene Terephthalate) (PET), Poly(Ethylene Naphthalate) (PEN), Poly(Ethylene Sulfate) (PES), PolyCarbonate (PC), Polyamide (PA), Polypropylene (PP), PolyVinyl Chloride (PVC), PolyTetraFluoroEthylene (PTTE), and/or a combination of them, amorphous, crystalline, oriented and non-oriented. Moreover, it can be applied and in all kinds of surface treatment with ion bombardment and with plasma, using all kinds of gases, such as Hydrogen ($H_2$), Nitrogen ($N_2$), Argon (Ar), Oxygen ($O_2$), Methane ($CH_4$) etc or a combination of them. The above apply for applications on static polymeric substrates and on large scale substrates for roll-to-roll and reel-to-reel applications.

The realization of measurements in such short time is in accordance with the one needed for the real-time control of thin films that are grown with deposition rate of ~5 Å/s, such as the $SiO_x$ thin films growth on a PET polymeric substrate.

Initially, a detailed description of the experimental unit for the in situ and real-time monitoring processes of optical properties during the processes of surface treatment and growth of thin films on polymeric substrate, as described above, will be given. Following, measurements realized for the presentation and use of the proposed technique, will be described.

B. Experimental Part

Figure 1:
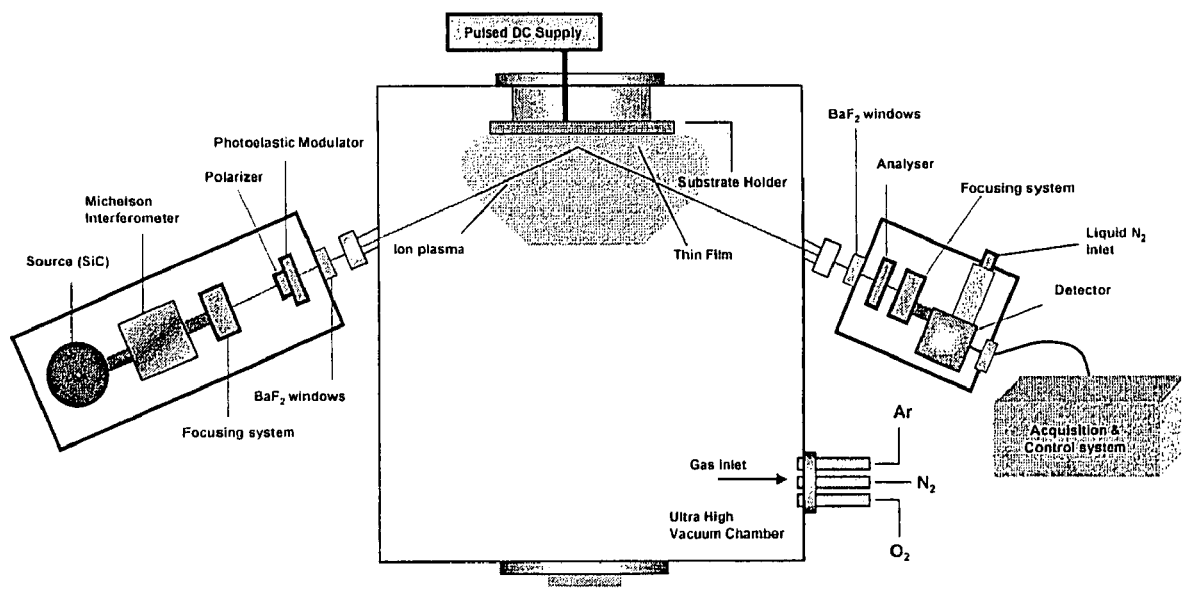
FIG. 1. Schematic representation of the in-situ Fourier Transform IR Spectroscopic Ellipsometer (FTIRSE) adjusted in a Ultra High Vacuum Chamber.

Spectroscopic Ellipsometry—SE measurements (FIG. 1) in the spectral region of Visible-Far Ultraviolet (Vis-FTV) were realised with a Fast MultiWavelength Ellipsometer (FMWE) unit that was developed in collaboration with Horiba/Jobin-Yvon, while the SE measurements in the spectra area of Infrared (IR) were realised with the Fourier Transform IR Spectroscopic Ellipsometer (FTIRSE) unit. Both units are adjusted on a ultra high vacuum chamber where the angle of incidence is 700. Other angles, lower or higher, from 700 can also be used. The chamber is equipped with various Physical Vapor Deposition techniques (PVD) while for the thin films growth on polymeric substrates is used the e-beam evaporation technique. The substrate holder on which the substrate is adjusted is positioned horizontally on stable position and it has the capability to rotate around a vertical axis.

The SE measurements are performed in the spectra are of the Visible-Far Ultraviolet (Vis-FUV) from 1.5-6.5 eV (190-830 nm), and in the spectra area of IR, 0.1-0.49 eV (900-4000 cm$^{-1}$). The realization of the measurements in the spectra area of Vis-FUV are applied for the study of the material's optical properties (bulk materials and thin films), that are related to the electronic transmissions, their electronic structure and their thickness. The real-time measurement is performed with the simultaneous acquisition of 32 different wavelengths. (32 simultaneously measured data points) that cover the energy range of 1.5-6.5 eV. The upper energy limit of SE spectra acquisition with the use of FMWE is 6.5 eV (190 nm), and with which can be performed the control of the polymeric membranes' and grown thin films optical properties. This is so, since the energy position of the maximum absorption is related directly to the stoichiometry and the higher the upper measurement energy limit, the more accurate is the determination of the absorption energy. The measurements in the IR spectral range are used for the study of the vibration modes and of the chemical bonding between atoms, that represent the materials studied, and of the thickness of the thin films that are formed either by the surface modification, either by their growth on the substrate. All provide comparable information on the materials composition and stoichiometry.[6]

Moreover, the deposition rates of the oxide films, that have been referred are significantly lower in comparison to the ones in industrial: scale, so the evaporation process on stable or moving substrate is more controllable and repeatable and the grown thin films show higher density values than the ones that are produced on moving substrates with the form of rolls (roll-to-roll) or in in-line roll-to-roll production on industrial scale.

However, these processes can be applied in an in-line constant production and industrial scale.

C. Theory

The parameterization and analysis of the measured pseudo-dielectric function $<\in(E)>=<\in_1(E)>+i<\in_2(E)>$ has been performed with the use of a geometrical model consisted by three phases (air/thin film/polymeric substrate) in which the determination of the optical properties of each phase has been realized with the modified Tauc-Lorentz (TL) model.[1]

In the case where the surface modification of the polymeric substrate is measured, the thin film represents the modified layer. In the TL model the imaginary part $\in_2(E)$ of the dielectric function is determined by multiplying the Tauc density of states with the $\in_2$ that results from the Lorentz oscillator model. Therefore, the TL model provides the capability of determining the fundamental optical gap Eg of the interband transitions, the energy E0, the broadening C and the strength A of each oscillator. The E0 of this model is correlated to the known Penn gap, the energy position where the strong electronic absorption of the material, mainly amorphous, takes place. The imaginary part $\pm\in_2(E)$ of the TL oscillator, for both amorphous and crystalline materials, is given by the following relations:

$$\varepsilon_2(E) = \frac{AE_0C(E-E_g)^2}{(E^2-E_0^2)^2+C^2E^2} \cdot \frac{1}{E}, E > E_g \quad (1)$$

$$\varepsilon_2(E) = 0, E \leq E_g, \quad (2)$$

and the real part $\in_1(E)$ is determined by Kramers-Kronig integration, by the relation:

$$\varepsilon_1(E) = \varepsilon_\infty + \frac{2}{\pi}P\int_{\varepsilon_1}^{\infty}\frac{\xi\varepsilon_2(\xi)}{\xi^2-E^2}d\xi, \quad (3)$$

whereas for E=0 is $$n^2(E=0) = \varepsilon_1(E=0) = \varepsilon_\infty + \frac{2}{\pi}\int_{E_1}^{\infty}\frac{\varepsilon_2(\xi)}{\xi}d\xi \quad (4)$$

The basic information deduced by SE measurements/analyses concerns the film thickness, and the optical parameters and constants, which are strongly related to films' stoichiometry and quality. More specifically, it can be calculated:

The energy where the maximum electronic absorption takes place for the $SiO_x$ namely the Penn Gap, $E_0$.

The value of the refractive index at zero energy n(E=0) which is relative to its density.

The fundamental band gap $E_g$.

The damping factor of the absorption peak attributed to electronic absorption; the broadening C.

The strength of the absorption peak A.

The $\in_\infty$ that measures the material strength and accounts the contribution of all electronic transitions, even those not taken into account in the modeling analysis, because they occur at high energies well above the experimental measured energy range, otherwise it is equal to unity.

Among the aforementioned calculated characteristic parameters the most important that are determined by the spectra analysis, are the Penn gap $E_0$ and the refractive index n.

The E0 is directly related to films' stoichiometry, whereas the n(E=0) is related to both films' stoichiometry and quality; such as the existence of microvoids and defects (Si inclusions). All the others parameters, such as the Eg, provides indirect information for the quality, composition, and stoichiometry of the deposited materials and/or the modified layers and substrates.

The use of the three phase model (air/thin film/polymeric substrate) for the analysis of the SE spectra or the FMWE measured spectra, that is deduced during the oxide deposition, provides the capability of determination of the thickness d of the inorganic and organic film. With this analysis it can be checked the stability and the effectiveness of the deposition processes.

Figure 2:
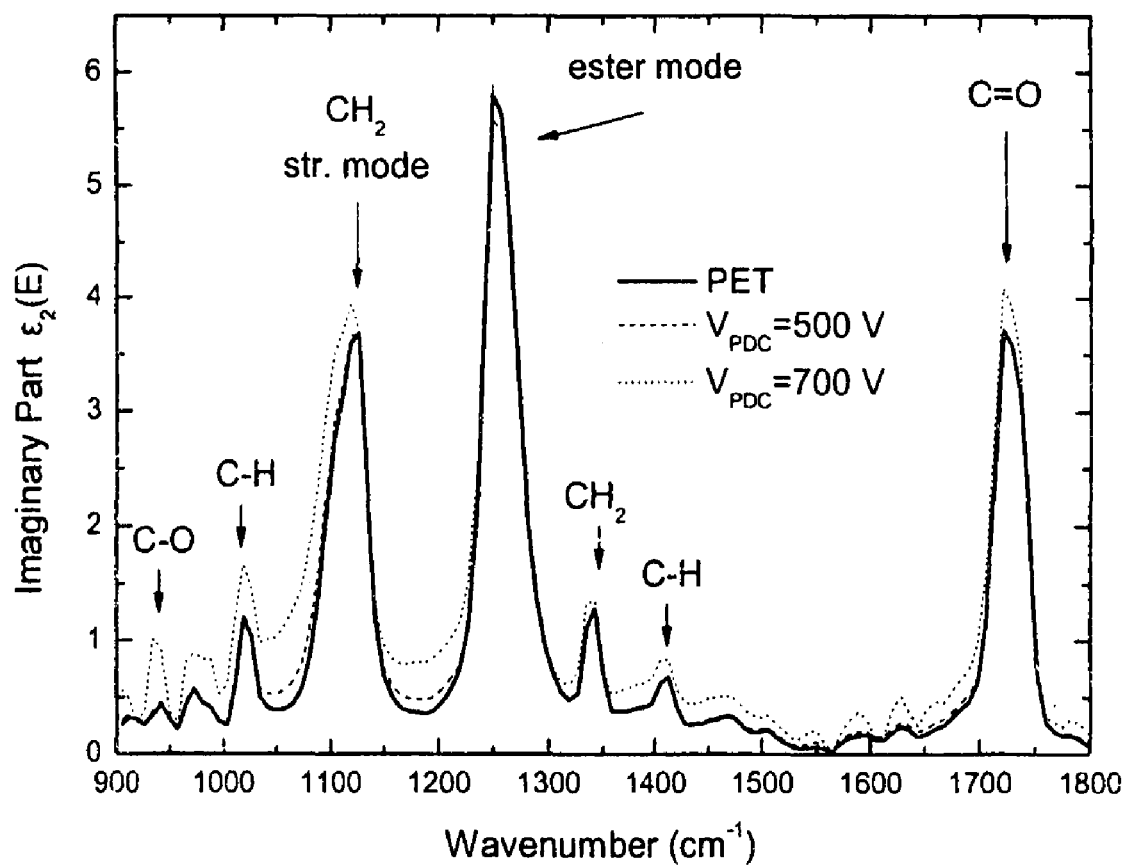
FIG. 2. Spectra of the imaginary part <$\in_2(E)$> of the dielectric function during the surface treatment of the polymeric substrate Poly(Ethylene Terephthalate) (PET) with Nitrogen ($N_2$) ion bombardment by Pulsed DC Plasma Etching.
Figure 3:
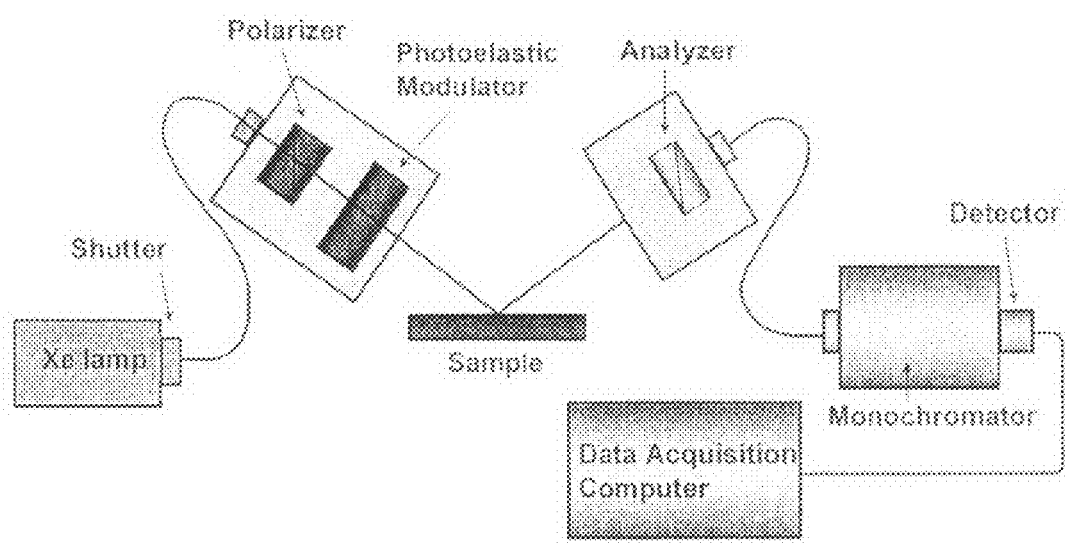
FIG. 3. Schematic representation of the ex-situ of Spectroscopic Ellipsometry unit of the near infrared (Near IR)—Visible-Far Ultraviolet (Visible-FUV) spectral region.

D. Measurement and Parameterization of the Optical Properties in Real-Time During the Surface Modification of Polymeric Membranes FIG. 2 shows the measurement of the optical properties by the use of FTIRSE in real-time, during the surface treatment of Poly(Ethylene Terephthalate) (PET) polymeric substrate with Nitrogen ($N_2$) atoms using Pulsed DC Plasma Etching. The partial pressure of the chamber was ~30 mTorr and the gas flow remained constant at 40 sccm, whereas the voltage applied on the substrate holder through the high voltage pulse modulator (Advanced Sparc-le V) was 700V with frequency of 100 Hz. The surface treatment process has duration of 20 min. In this figure the imaginary part $<\in_2(E)>$ is presented.

E. Measurement and Parameterization of the Optical Properties in Real-Time During the Growth of Thin Films onto Polymeric Membranes.

Figure 4:
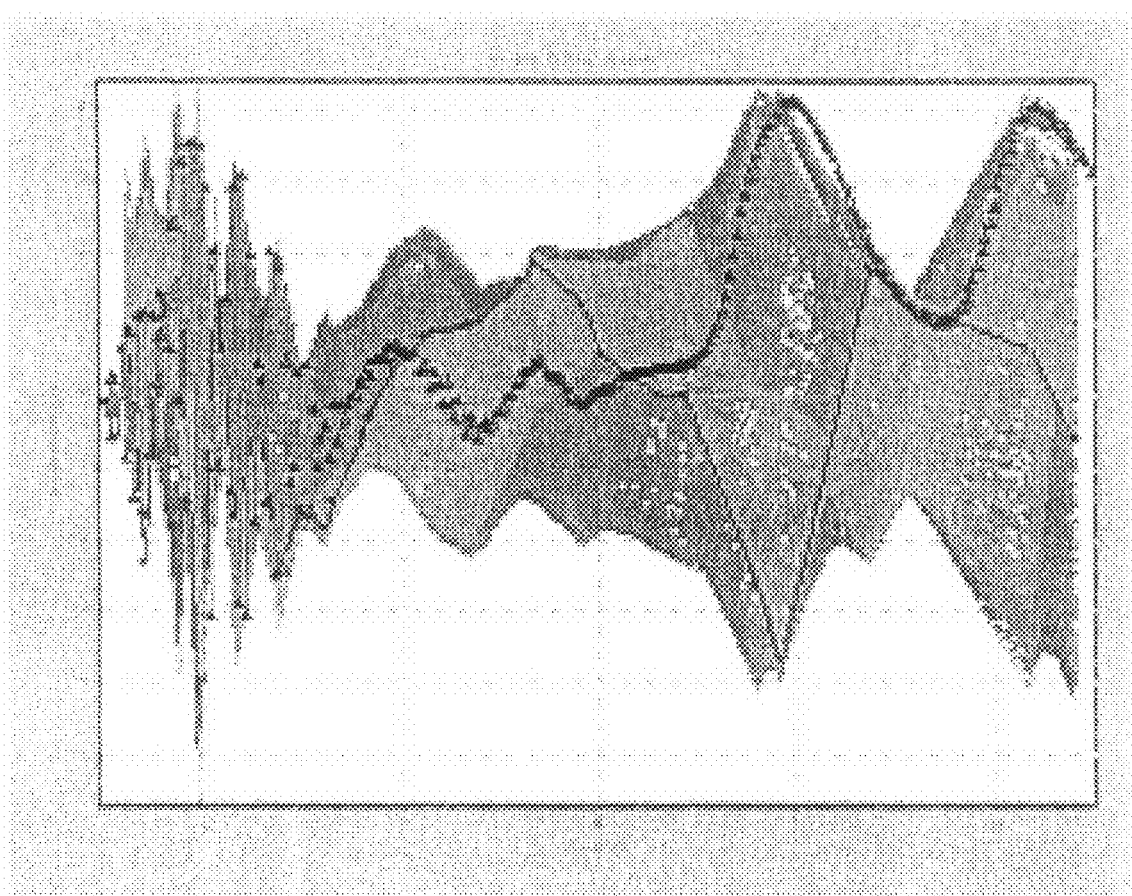
FIG. 4. The <$\in_2(E)$> spectra in real-time during $SiO_2$ thin film growth on polymeric substrate PET, with e-beam evaporation technique and with the evaporation $SiO_2$ material. The triangles correspond to the measured imaginary part $<\epsilon_2(E)>$ of PET before the $SiO_2$ deposition, while the circles correspond to the $<\epsilon_2(E)>$ of $SiO_2$.
Figure 5:
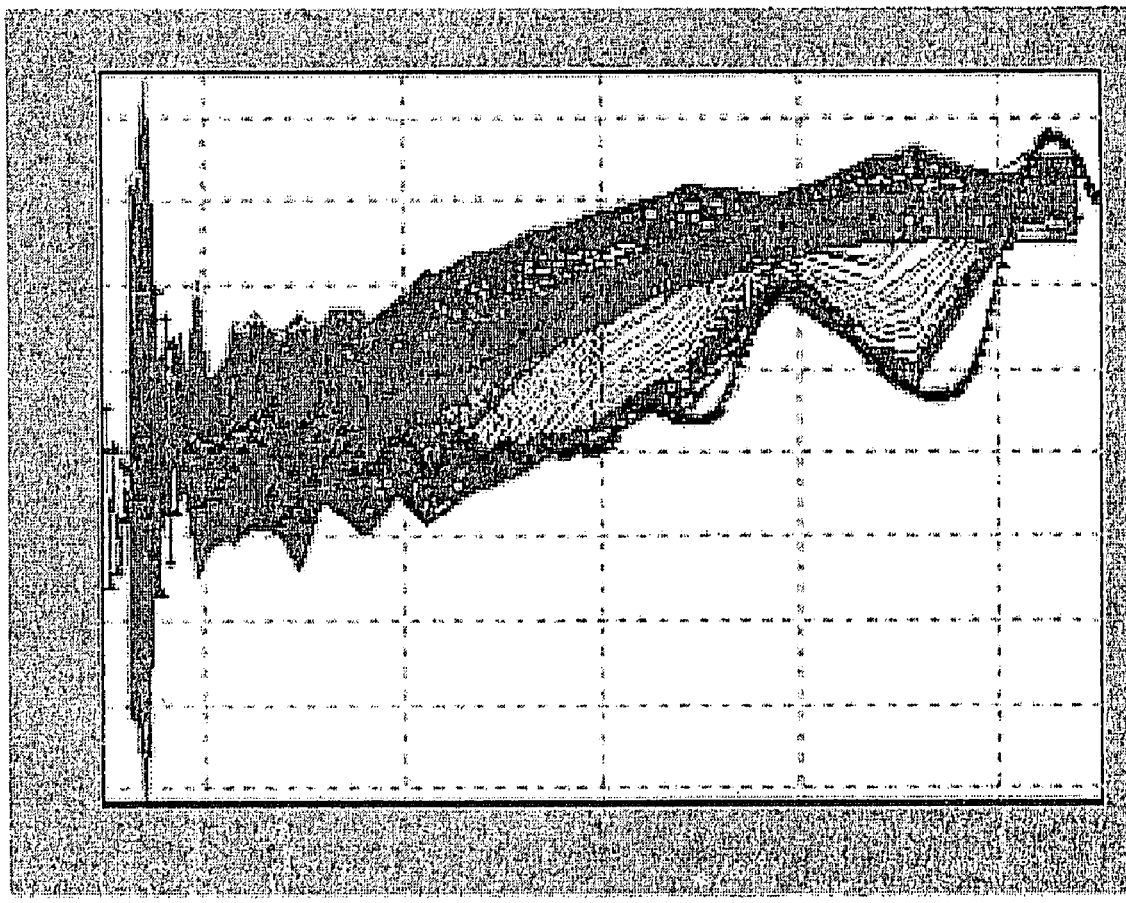
FIG. 5. The $<\epsilon_2(E)>$ spectra in real-time during SiO thin film growth on polymeric substrate PET, with e-beam evaporation technique and with the evaporation of SiO material. The triangles correspond to the measured imaginary part $<\epsilon_2(E)>$ of PET before the SiO deposition, while the circles correspond to the $<\epsilon_2(E)>$ of SiO.
Figure 6:
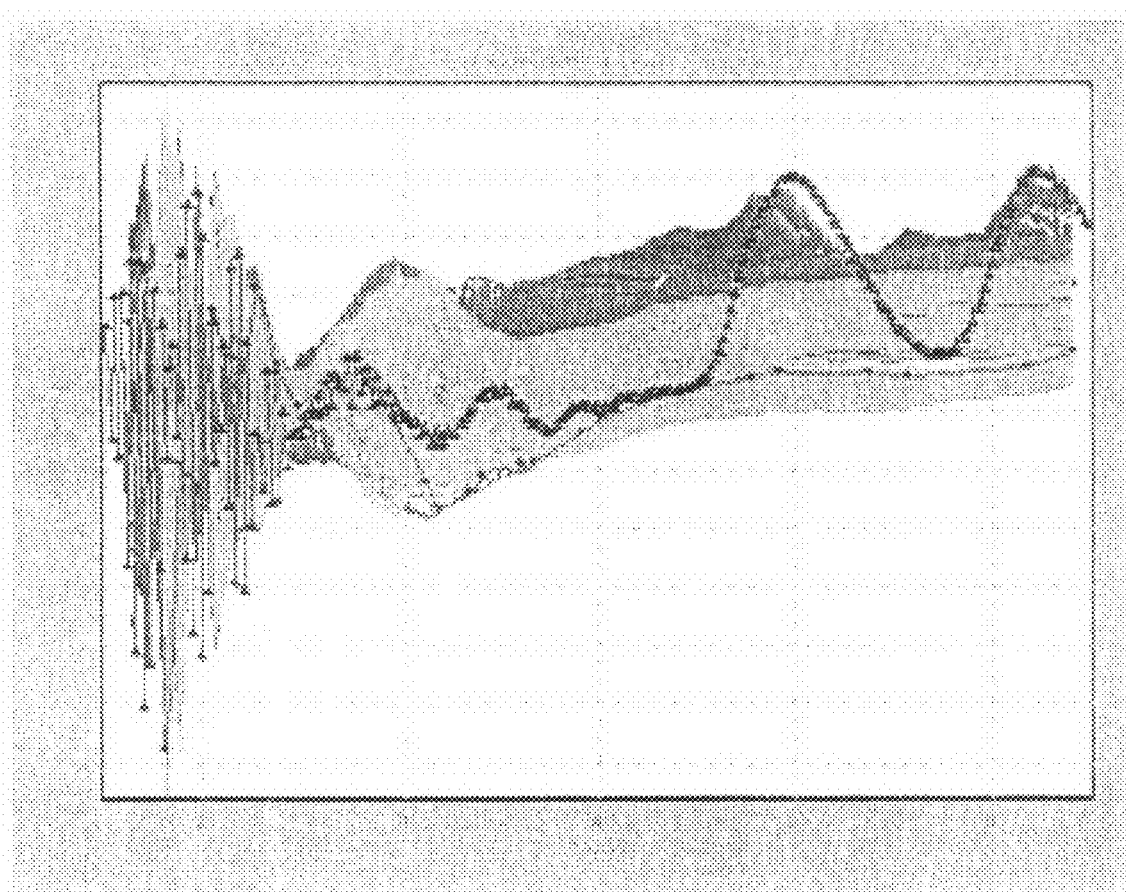
FIG. 6. The $<\epsilon_2(E)>$ spectra in real-time during $SiO_x$ thin film growth on polymeric substrate PET, with e-beam evaporation technique and with the evaporation mixed SiO and $SiO_2$ material. The triangles correspond to the measured imaginary part $<\epsilon_2(E)>$ of PET before the $SiO_x$ deposition, while the circles correspond to the $<\epsilon_2(E)>$ of $SiO_x$.

FIGS. 4, 5 and 6 show the in-situ and real-time control of the optical properties during the growth of $SiO_x$ thin films onto PET polymeric substrate with electron beam evaporation of $SiO_2$, SiO and mixed SiO and $SiO_2$, for achievement of the intermediate stoichiometry, respectively. In these figures it is presented the imaginary part $<\in_2(E)>$. The thin films growth has been realized in sequential layers with total time of 450 s and for the real-time SE measurements the Sampling Time (time between two sequential measurements) was ST=1 s.

Figure 7:
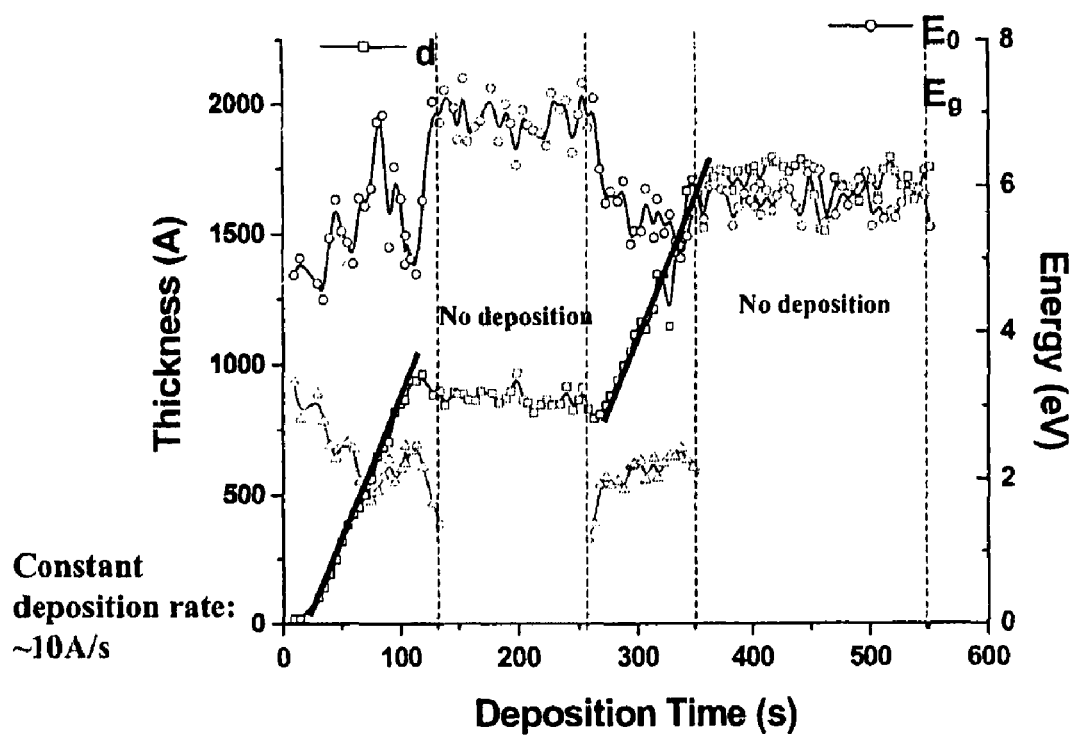
FIG. 7. Time dependence of the thickness, the Penn gap $E_0$ and the energy gap $E_g$ of the $SiO_x$ thin film grown on the PET polymeric, substrate. The results were obtained with the real-time analysis of the SE spectra measured by the FMWE unit.
Figure 8:
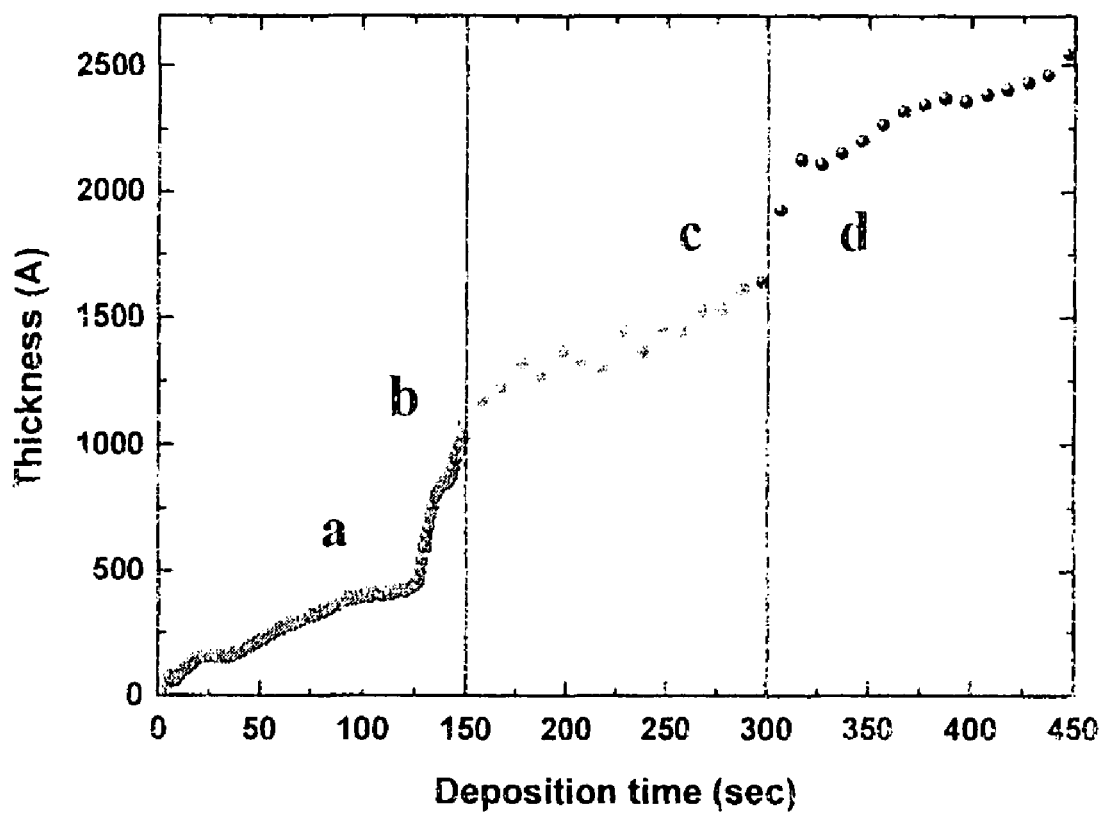
FIG. 8. Time dependence of the thickness of the $SiO_x$ thin film grown on the PET polymeric substrate by electron beam evaporation of SiO. The results were obtained with the real-time analysis of the SE spectra measured by the FMWE unit.
Figure 9:
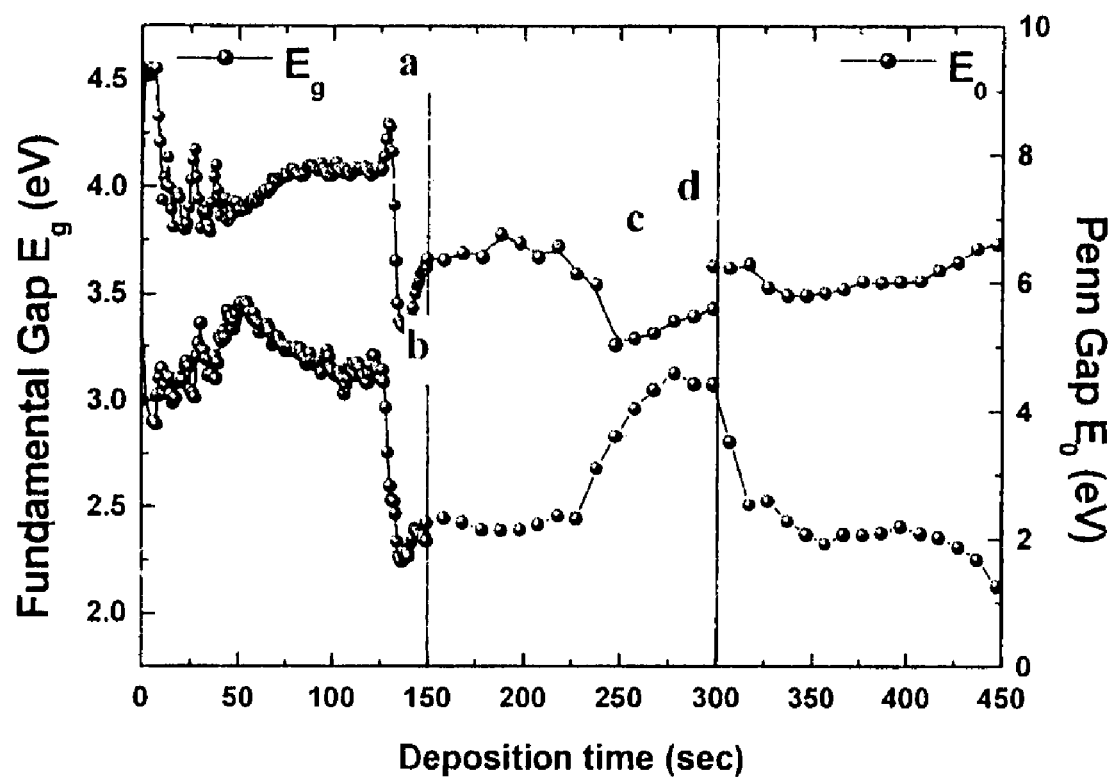
FIG. 9. Time dependence of the Penn gap $E_0$ and the energy gap $E_g$ of the $SiO_x$ thin film grown on the PET polymeric substrate by electron beam evaporation of SiO. The results were obtained with the real-time analysis of the SE spectra measured by the FMWE unit.

By the analysis of the SE spectra with the Eq. (1)-(4) in combination with the three phase model (air/thin film/polymeric substrate), the thickness d of the $SiO_x$ thin film deposited onto PET can be determined. FIG. 7 shows an example of the determination of thickness d as a function of the deposition time during the sample rotation, form which we can evaluate and control in-line the deposition process stability and effectiveness. Thus, when the thickness d is constant with time, the deposition process does not occur, since the evaporated material transport is interrupted. When this transport is restored, we have an almost linear deposition rate (~10 Å/s) at the initial stages and a linear deposition rate for stable deposition conditions. The change of the deposition conditions affects the deposition rate of the $SiO_x$ thin films, as it can be seen at the points a, b, c and d in FIGS. 8 and 9. The information that is obtained from the analysis of the measured SE spectra, in-situ and real-time is very important for industrial scale.

As already it has been reported, the $E_0$, $E_g$ and the refractive index n(E=0) are related directly with the stoichiometry and the quality (which are basic intermediate properties). These, depend with other final functional properties of materials, such as for example with the barrier properties of thin films $SiO_x$ and $SiN_x$.

The determination of these parameters in real-time is realized with the modelling process that was described above and it is shown in FIG. 9. From this figure, we observe that for the first the 100 s, the optical properties of the grown thin film show higher divergences. This can be attributed in the instabilities of the deposition process since the evaporation material is the mixed ($SiO_2$+SiO). Also, in FIG. 5 it can be seen the change of $E_0$ and $E_g$ parameters, as they were determined with analysis of the SE spectra in real-time. The stoichiometry shows changes with the deposition time due to corresponding changes in the growth conditions. Consequently, the characteristics and the quality of the grown films can be controlled in real-time with the suitable modifications in the applied experimental conditions.

Correlation Between the Optical and the Intermediate and Final Functional Properties.

The Penn gap $E_0$ exhibits a monotonic increase and an almost linear correlation with the stoichiometry (e.g. $SiO_x$). In the case of silicon monoxide SiO (having an x=1) it is $E_0$=5.6 eV, whereas for silicon dioxide $SiO_2$ (having an x=2) it is $E_0$=12 eV.

In the literature there are two available values of $E_0$ for $SiO_2$ depending on its amorphous or crystalline microstructure that is 10.5 and 12 eV, respectively. In a first approximation the $E_0$ is correlated to stoichiometry depending on the amorphous or crystalline microstructure of the films is given by the following relations:

$$E_0^{amorphous}(x)=5.6+(x-1)\cdot 4.9 \text{ eV}, \quad (4)$$

$$E_0^{crystalline}(x)=5.6+(x-1)\cdot 6.4 \text{ eV}. \quad (5)$$

Figure 10:
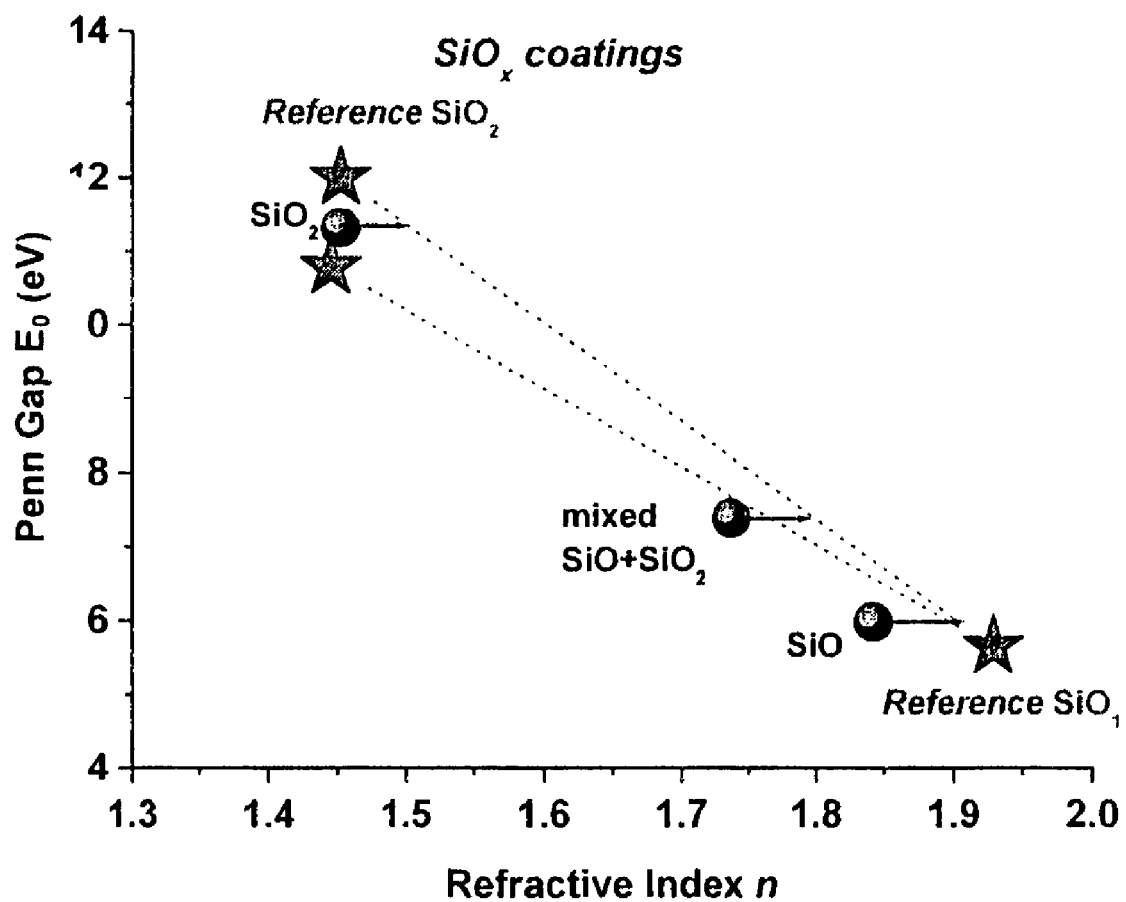
FIG. 10. Correlation of the optical parameters $E_0$ and n(E=0) of $SiO_x$ thin films that were grown with the e-beam evaporation technique in stable polymeric substrates. For comparison reasons reference data for stoichiometric SiO2 and SiO have been included.

In FIG. 10 are shown the points that correspond in determined parameters $E_0$ and n(E=0) of representative $SiO_x$ thin films with the points that correspond to the stoichiometric materials $SiO_2$ and SiO. According to the above relations (4) and (5), the stoichiometry of a thin film that is characterized by specific $E_0$ and n(E=0) values will be found in some point of the straight line that links the corresponding points. Thus, with the determination of $E_0$ from the analysis of the SE spectra that was described above, we can calculate the stoichiometry x of the grown thin films. This methodology provides accurate results, rendering suitable for the characterization and the control of the properties and the quality of thin transparent films, inorganic and organic materials that are developed in polymeric substrates or other transparent substrates.

The final functional properties of the thin films do not depend only on the stoichiometry but also on their quality, which can be evaluated by the refractive indices values, (n(E=0)), which depend on stoichiometry and on other structural and compositional properties such as microvoids, surface roughness, cracks or inclusions.

Figure 11:
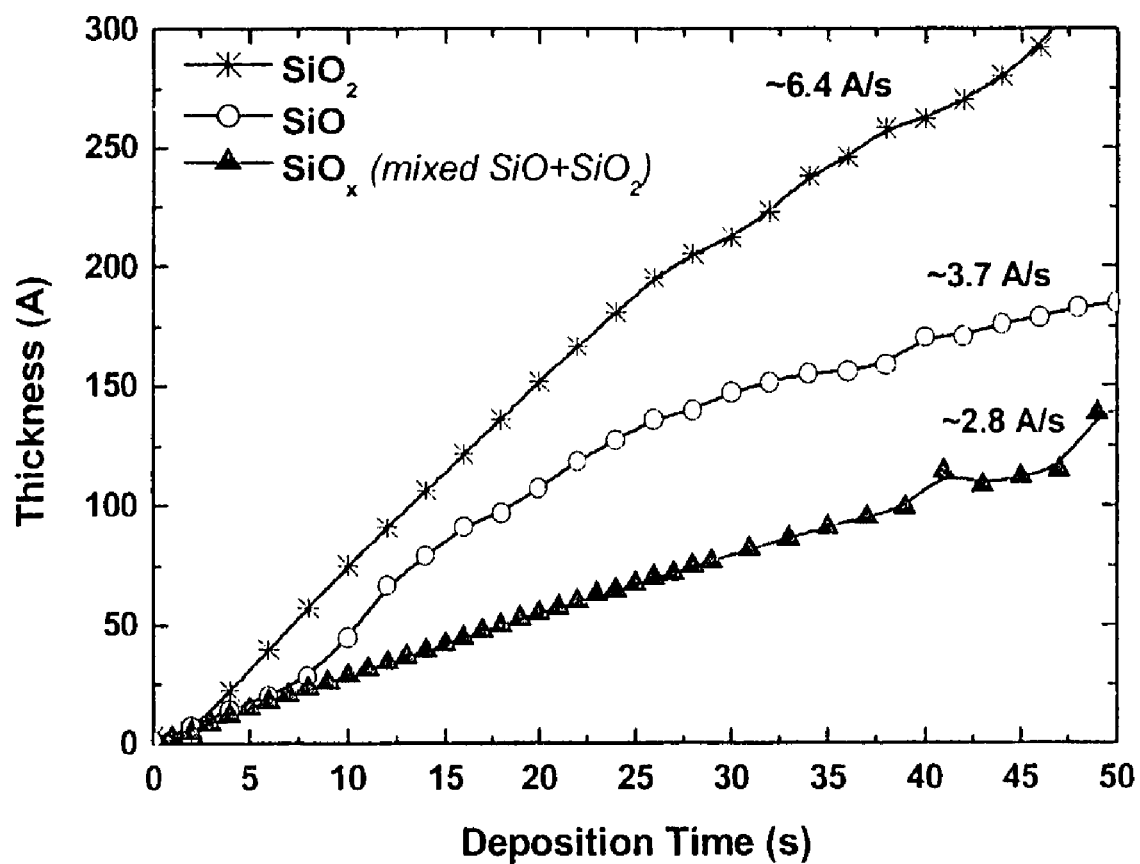
FIG. 11. Evolution of the thickness of $SiO_2$, SiO and $SiO_x$ films during the first 50 s of their growth process.

FIG. 11 shows the comparative results from the real-time analysis of SE spectra in the Vis-FUV spectral region, from three $SiO_x$ thin films that were deposited onto polymeric substrate (PET) by electron beam evaporation of three different materials $SiO_2$, SiO, and $SiO_x$ (mixed SiO+$SiO_2$). From this figure we observe the dependence of thickness as a function of deposition time from which we conclude that in small thicknesses the nucleation and coalescence stages take place, which are followed by the homogenous growth stage. From this dependence we can determine the deposition rate of the each film (6.4, 3.7 and 2.8 Å/s, for $SiO_2$, SiO and $SiO_x$, respectively).

Figure 12:
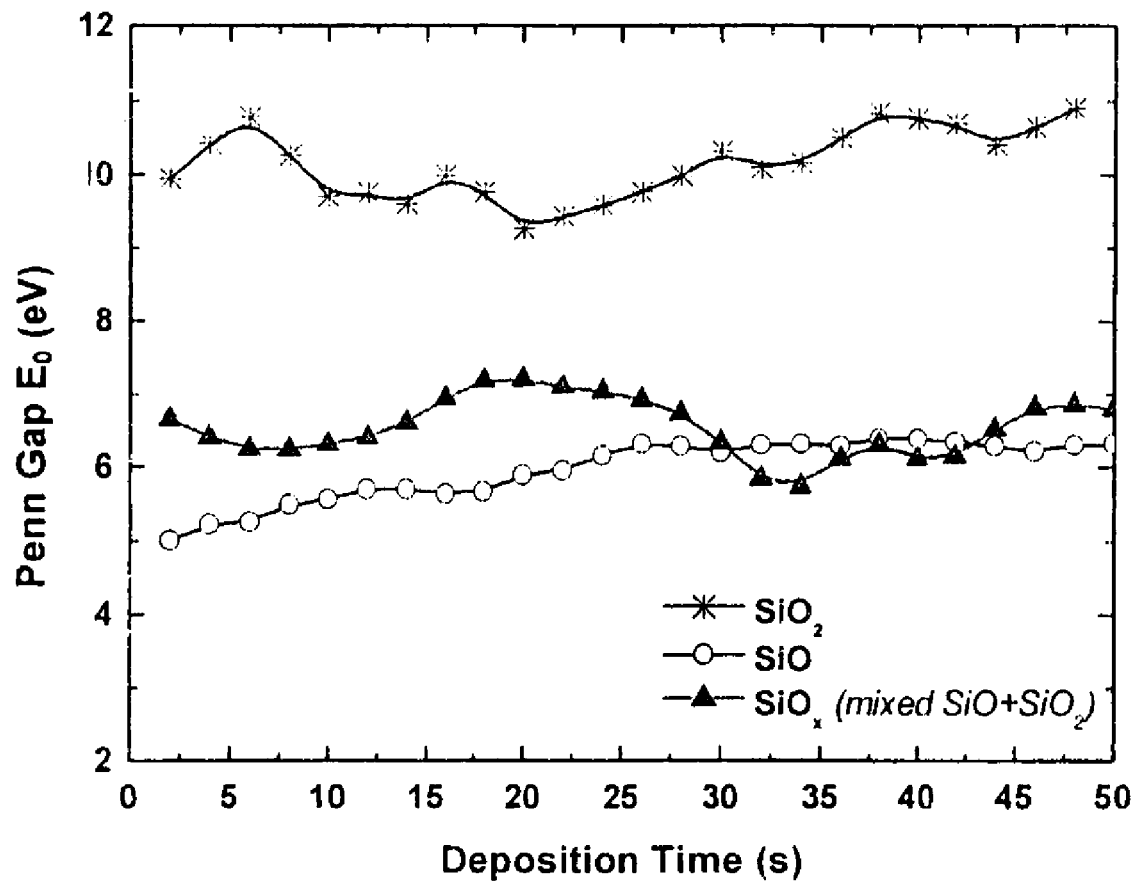
FIG. 12. Evolution of $E_0$ of $SiO_2$, SiO and $SiO_x$ films during the first 50 s of their growth process.
Figure 13:
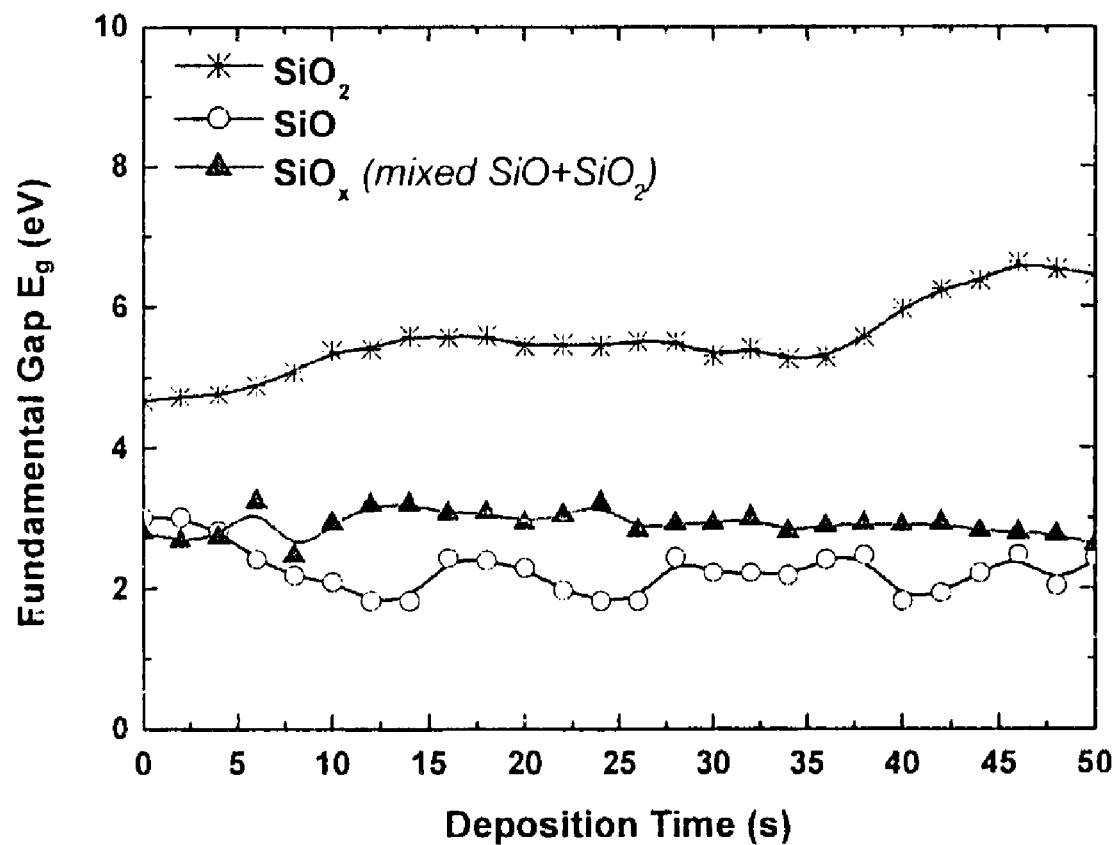
FIG. 13. Evolution of $E_g$ of $SiO_2$, SiO and $SiO_x$ films during the first 50 s of their growth process.

FIGS. 12 and 13 show the evolution of the $E_0$ and $E_g$ parameters with the deposition time, as determined with the above methodology.

Figure 14:
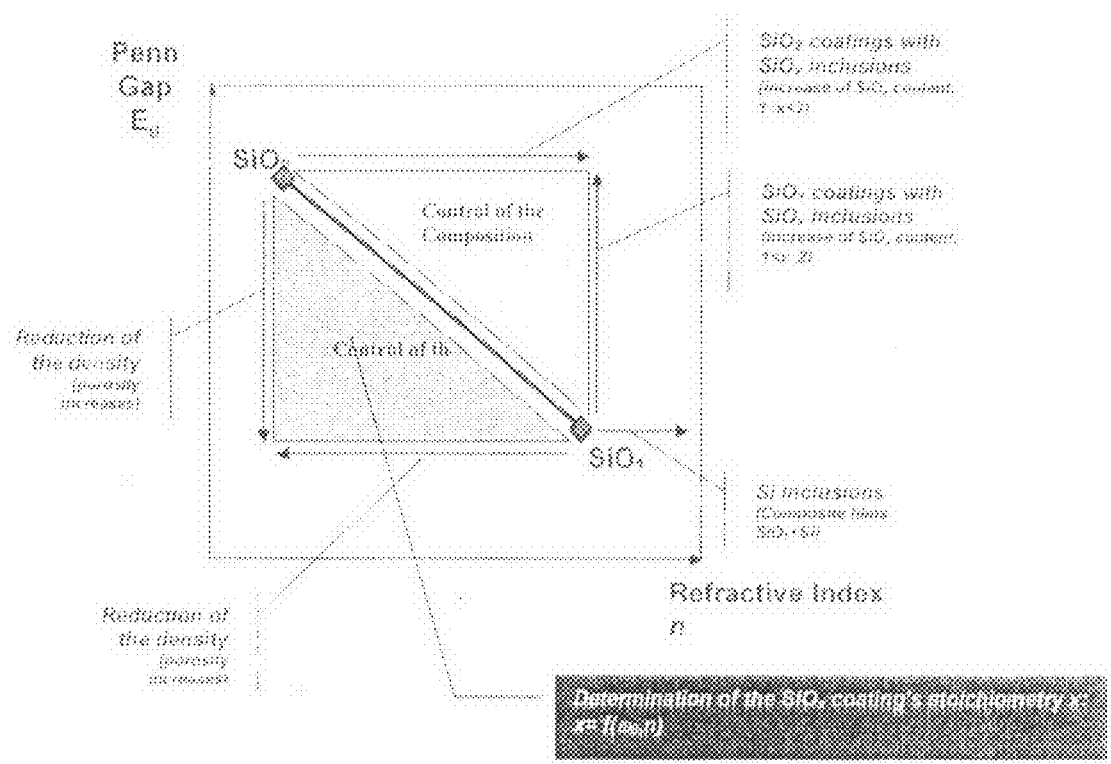
FIG. 14. Correlation of the optical properties $E_0$, n (E=0) of $SiO_x$ films and of the stoichiometry, composition and quality.

The determination of the barrier properties for gases and water vapours of the $SiO_x$/PET system is accomplished with the correlation the optical and other properties of system, that were measured in real-time with the above methodology (e.g. stoichiometry x), with the penetrability measurements for oxygen (OTR) and water vapours (WVTR). For the deduction of accurate conclusions, we use the refractive index n(E=0) and the Penn gap $E_0$, otherwise it is difficult to correlate the optical and the final functional properties. These are shown in FIG. 14.

Consequently, the in-situ and real-time determination of the optical properties and the quality is particularly important and leads to direct determination of final functional properties of these systems (inorganic thin films on polymeric substrates) at their growth, something that it is impossible to become with other techniques. Also, with this methodology becomes possible, with the tuning and adjustment of the e experimental growth conditions, the growth of materials on polymeric substrates with the desirable functional properties that are essential for the each application. The knowledge of final functional properties in real-time at the growth of these systems, as it is affected by the change of the deposition conditions is very important in industry, particularly since it can be used in moved substrates and in in-line production, making this methodology essential for use in industrial scale.

The invention claimed is:

1. A method for real-time monitoring and determination of the thickness, optical properties and quality of thin films of transparent inorganic and organic materials during their growth process on polymeric substrates, comprising:
   (a) multiple ellipsometric measurements taken simultaneously at different wavelengths in the energy region from violet to far ultraviolet, where the transparent inorganic and organic materials exhibit their optical absorption peaks;
   (b) simultaneous ellipsometric measurement of at least 32 different wavelengths, that represent a pseudo-dielectric function spectra, in the violet - far ultraviolet energy region, collected in a short time in the range of ms, using a multiwavelength ellipsometer unit;
   (c) parameterization and analysis of the measured pseudo-dielectric function with the use of a geometrical model of an air/thin film(s)/substrate, for the calculation of the wavelength dependent optical parameters of each film, thus providing the Penn gap $E_0$, energy gap $E_g$, refractive index n(E=0), thickness and deposition rate of the transparent thin film grown on the polymeric substrates;
   (d) calculation of the stoichiometry x of oxides, nitrides and composition through the Penn gap or mean gap $E_0$, and of the stoichiometry, composition and quality of the thin films grown on the polymeric substrates that are related to the refractive index n(E=0); and
   (e) determination of the barrier and reflective properties of the transparent thin films grown on the polymeric substrates through the optical properties of Penn gap $E_0$, energy gap $E_g$ and refractive index n(E=0).

2. A method according to claim 1; including determination of the barrier properties in gases and vapors, which are the Oxygen Transmission Rate (OTR) and Water Vapor Transmission Rate (WVTR), of the system thin film(s)/polymeric substrate through the optical properties and the stoichiometry, composition and quality of the transparent inorganic and organic thin films grown on polymeric substrates.

3. A method according to claim 1; wherein the optical properties of each thin film are calculated using the modified Tauc-Lorentz model (TL).

* * * * *